US008076505B2

(12) United States Patent
Folleas et al.

(10) Patent No.: US 8,076,505 B2
(45) Date of Patent: Dec. 13, 2011

(54) PROCESS OF PREPARING DERIVATIVES OF 1-(2-HALOBIPHENYL-4-YL)-CYCLOPROPANECARBOXYLIC ACID

(75) Inventors: Benoit Folleas, Parma (IT); Hubert Botte, Parma (IT); Thomas Delacroix, Parma (IT); Fausto Pivetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 240 days.

(21) Appl. No.: 12/466,660

(22) Filed: May 15, 2009

(65) Prior Publication Data

US 2009/0312426 A1    Dec. 17, 2009

(30) Foreign Application Priority Data

Jun. 11, 2008  (EP) ..................... 08158022

(51) Int. Cl.
*C07C 61/04* (2006.01)
*C07C 255/00* (2006.01)

(52) U.S. Cl. ....................... 562/506; 558/434
(58) Field of Classification Search .......... None
See application file for complete search history.

(56) References Cited

U.S. PATENT DOCUMENTS 7,662,995 B2 * 2/2010 Raveglia et al. ............. 562/499
2009/0291988 A1 * 11/2009 Oballa ......................... 514/357

OTHER PUBLICATIONS

Peretto et al., J. Med. Chem 2005, 48, 5705-5720.*
U.S. Appl. No. 12/846,341, filed Jul. 29, 2010, Pivetti, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

Compounds represented by formula (I):

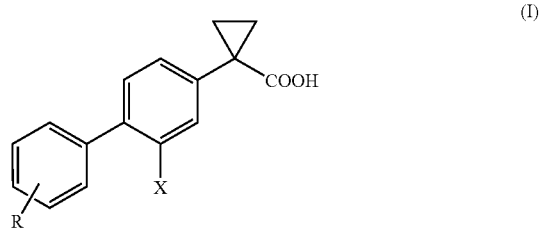

may be conveniently prepared by a process in which a Suzuki reaction is performed as an early step.

14 Claims, No Drawings

PROCESS OF PREPARING DERIVATIVES OF 1-(2-HALOBIPHENYL-4-YL)-CYCLOPROPANE-CARBOXYLIC ACID

CROSS REFERENCES TO RELATED APPLICATIONS

This application claims priority to European Patent Application No. 08158022.7, filed on 11 Jun. 2008, which is incorporated herein by reference in its entirety.

BACKGROUND OF THE INVENTION

1. Field of the Invention

The present invention relates to processes for preparing compound represented by formula (I) and pharmaceutically acceptable salts thereof:

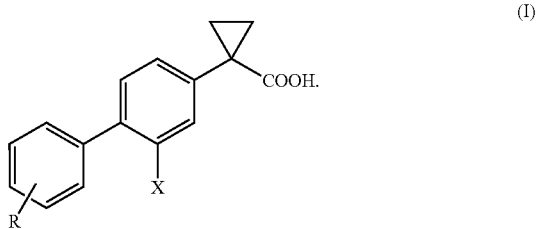

The present invention also relates to intermediates which are useful in the process.

2. Discussion of the Background

Alzheimer's disease is a neurodegenerative disorder characterized from a histopathologic point of view by a diffuse presence of extracellular and perivascular neuritic plaques and intracellular neurofibrillary tangles in the cerebral parenchyma of Alzheimer patients. Neuritic plaques are mainly composed of aggregates of a protein with 39-43 amino acid residues known as β-amyloid (βA), and, depending on the numbers of amino acids, $A\beta_{39}$, $A\beta_{40}$, $A\beta_{42}$ and $A\beta_{43}$.

Compounds have been reported which can reduce the production of the most neurotoxic isoform of β-amyloid, namely the form containing 42 amino acids ($A\beta_{42}$), through their interaction with a macromolecular/multiprotein enzymatic complex with aspartyl-protease activity, known as γ-secretase. In particular WO 2004/074232 discloses derivatives of 1-(2-halobiphenyl-4-yl)-cyclopropanecarboxylic acid of general formula (I):

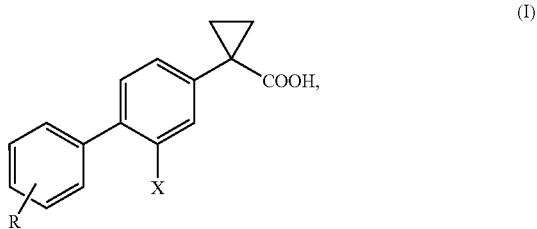

wherein X and R are defined below, which are capable of modulating γ-secretase activity without affecting other important metabolic processes such as cyclooxygenase-enzymes activity.

The key step of the preparation of said compounds is the Suzuki reaction between a suitable phenylboronic acid or an ester thereof with a 3,4-dihalo-cyclopropane-carboxylic acid. In WO 2004/074232, 3,4-dihalo-cyclopropanecarboxylic acid is obtained starting from 3,4-dihalo-toluene which is transformed into the corresponding benzylbromide by radical bromination in carbon tetrachloride ($CCl_4$); the resulting bromide is transformed into the 3,4-dihalophenylacetonitrile; the latter one is reacted with 1,2-dibromoethane to give the corresponding 3,4-dihalophenylcyclopropanenitrile which is finally hydrolyzed to the desired 3,4-dihalo-cyclopropanecarboxylic.

However, the process described in WO 2004/074232 gives rise to a low overall yield (12-14%) and suffers from severe restrictions for the industrial use. For example, the radical bromination step gives rise to a significant amount of the bis-halogenated side-product, detrimental to its yield, and involves the use of $CCl_4$ which is highly toxic and also both ozone-depleting and a greenhouse gas. In addition, the final Suzuki coupling reaction has a poor yield and the resulting product is difficult to purify by crystallization without a loss of yield. For example, silica gel chromatography has been used for such purification, but scale-up of silica gel chromatography is tedious and requires large volumes of solvents.

Thus, there remains a need for an alternative process of making 1-(2-halobiphenyl-4-yl)-cyclopropanecarboxylic acid compounds of formula (I).

SUMMARY OF THE INVENTION

Accordingly, it is one object of the present invention to provide novel processes of making 1-(2-halobiphenyl-4-yl)-cyclopropanecarboxylic acid compounds of formula (I).

It is another object of the present invention to provide novel processes of making 1-(2-halobiphenyl-4-yl)-cyclopropanecarboxylic acid compounds of formula (I) which do not suffer from the drawbacks mentioned above.

It is another object of the present invention to provide novel intermediates which are useful in such processes.

These and other objects, which will become apparent during the following detailed description, have been achieved by the inventors' discovery that by carrying out the Suzuki reaction as the first step 1-(2-halobiphenyl-4-yl)-cyclopropanecarboxylic acid compounds of formula (I) can be efficiently prepared.

Moreover, different conditions for ameliorating the yield of the other steps have been introduced, in particular the radical bromination step.

Thus, the process of the present invention is more efficient, especially for large scale production, providing a higher yield of the compounds of formula (I) in high chemical purity without the need for a chromatographic purification step.

Thus, the present invention provides:
(1) a process for preparing a compound of general formula (I) or a pharmaceutically acceptable salt thereof:

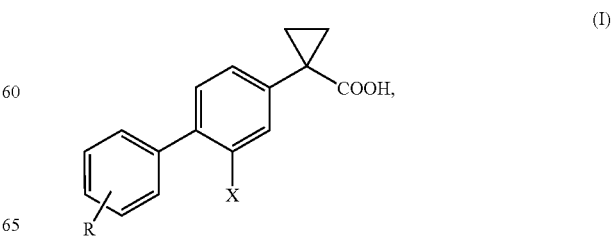

wherein:

X is a halogen atom, preferably fluorine;

there may be from 1 to 5 R substituents present and each R independently represents a group selected from halogen atoms, preferably chlorine;

—$CF_3$;

—$CH=CH_2$;

—CN;

—$CH_2OH$;

—$NO_2$;

methylenedioxy;

ethylenedioxy;

cycloalkyl, preferably $C_3$-$C_6$ cycloalkyl;

phenyl;

—$OR_1$ or —$NHCOR_1$, wherein $R_1$ is selected from the group consisting of —$CF_3$, alkenyl, alkynyl, benzyl, and phenyl;

—$SR_2$, —$SOR_2$, or —$COR_2$, wherein $R_2$ is alkyl;

said process comprising:

(i) reacting a compound of formula (II):

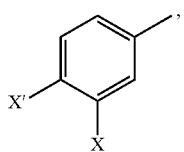

(II)

wherein X is defined as above and X' is chlorine, bromine, iodine or a triflate group ($CF_3SO_3$) with a compound of formula (III):

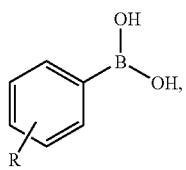

(III)

wherein R is defined as above, to obtain a compound of formula (IV):

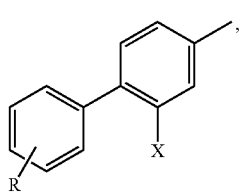

(IV)

wherein X and R are defined as above;

(ii) submitting said compound of formula (IV) to radical bromination to obtain a compound of formula (V):

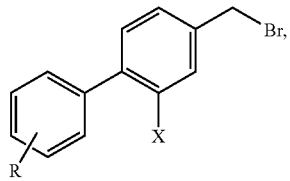

(V)

wherein X and R are defined as above;

(iii) converting said compound of formula (V) into a nitrile compound of formula (VI):

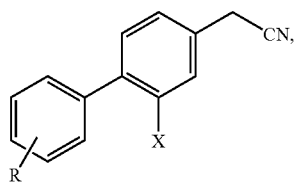

(VI)

wherein X and R are defined above;

(iv) reacting said compound of formula (VI) with 1,2-dibromoethane to obtain a compound of formula (VII):

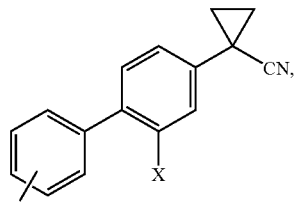

(VII)

wherein X and R are defined as above; and (v) hydrolyzing said compound of formula (VII) to obtain said compound of formula (I) or pharmaceutically acceptable salt thereof.

In a preferred embodiment, the radical bromination is conducted with N-bromosuccinimide (NBS) in the presence of a catalytic amount of benzoyl peroxide ($PhCOO)_2$) and acetonitrile as a solvent.

The present invention also provides the compounds of formula (VII), which have been obtained as stable intermediate of the reaction described above.

The invention further provides a process for preparing a pharmaceutical composition, said process comprising steps (i) to (v) and an additional step (vi) comprising admixture of one or more pharmaceutically acceptable excipients with a compound of formula (I) or a pharmaceutically acceptable salt thereof.

DETAILED DESCRIPTION OF THE PREFERRED EMBODIMENTS

Terms used in the specification have the following meanings:

As used herein, the term "halogen atoms" includes fluorine, chlorine, bromine, and iodine.

As used herein, "alkyl" means straight chain or branched $C_1$-$C_4$ alkyl, such as methyl, ethyl, n-propyl, isopropyl, n-butyl, isobutyl, sec-butyl, and tert-butyl.

As used herein "alkenyl" means straight chain or branched $C_2$-$C_6$ alkenyl, such as vinyl, 1-propenyl, 2-propenyl, 1-butenyl, isobutenyl, or straight- or branched-pentenyl and hexenyl. The term "alkynyl" is to be construed in an analogous manner.

As used herein, "cycloalkyl" means a cyclic non-aromatic hydrocarbon group containing from 3 to 8 carbon atoms. Examples include cyclopropyl, cyclobutyl, cyclopentyl, cyclohexyl and cycloheptyl.

As used herein "saturated heterocyclic" means a saturated heterocyclic group having at least 4 carbon atoms and at least one heteroatom, preferably from one to four heteroatoms selected from nitrogen, oxygen, and sulphur. Examples include piperidyl or tetrahydrofuryl.

Thus, in a first embodiment, the present invention provides novel processes for preparing a compound of formula (I):

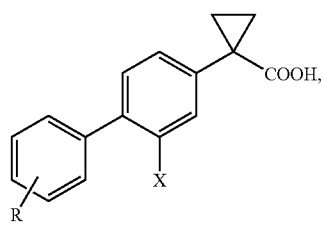

(I)

wherein X and R are as defined earlier.

When R is cycloalkyl, said ring is optionally substituted with one or more groups independently selected from alkyl, —$CF_3$, —OH, and oxo groups. Preferably the cycloalkyl group is $C_3$-$C_6$ cycloalkyl.

When R is phenyl, said ring is optionally substituted with one or more groups independently selected from halogen atoms, —$CF_3$, —$OCF_3$, —OH, alkyl, and a saturated heterocyclic. The saturated heterocyclic group is preferably a monocyclic ring having 5 or 6 atoms and one or two nitrogen atoms or one nitrogen atom and one oxygen atom such as pyrrolidine, imidazolidine, and isoxazolidine.

One embodiment of the present process is shown below in Scheme I.

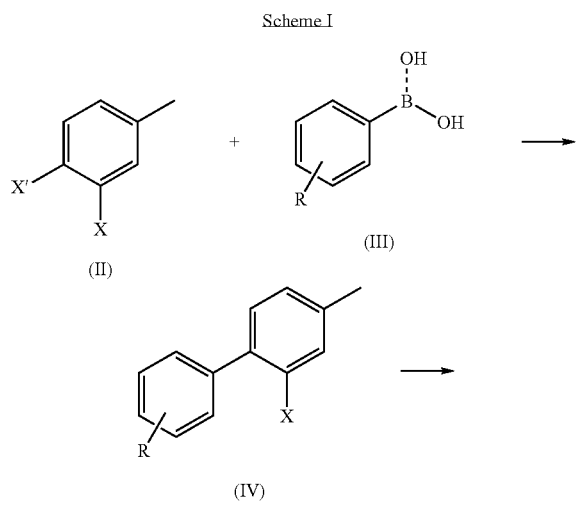

Scheme I

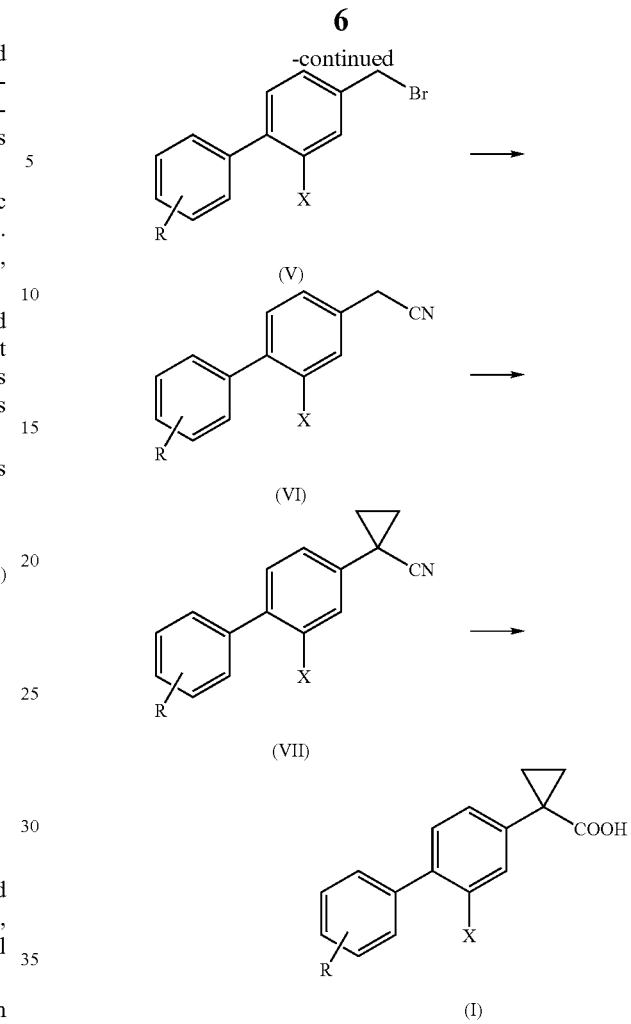

In the first step (step i), a compound having formula (II), wherein X is a halogen atom, preferably fluorine and X' is selected from the group consisting of chlorine, bromide, iodine, and a $CF_3SO_3$ group (triflate), is reacted with a phenyl boronic acid of formula (III), wherein R represents one or more groups independently selected from halogen atoms, preferably chlorine; —$CF_3$; —CH=$CH_2$; —CN; —$CH_2$OH; —$NO_2$; methylenedioxy; ethylenedioxy; cycloalkyl; phenyl; —$OR_1$ or —$NHCOR_1$ (wherein $R_1$ is selected from the group consisting of —$CF_3$, alkenyl, alkynyl, benzyl, and phenyl; and —$SR_2$, —$SOR_2$, or —$COR_2$ (wherein $R_2$ is alkyl).

The compounds of formulae (II) and (III) are commercially available or may be prepared according to methods well known to the skilled person.

Preferably the reaction, known as the Suzuki reaction or Miyaura-Suzuki reaction is carried out using 4-bromo-3-fluoro-toluene as the compound of formula (II) and 3,4-dichloro-phenylboronic acid as the compound of formula (III).

Said reaction, which relies on a palladium catalyst, also be carried out using an alkyl boronic ester instead of a boronic acids.

Advantageously, any palladium catalyst such as for example tetrakis(triphenyl-phosphine)palladium [Pd(PPh)$_3$], palladium on activated charcoal also known as Palladium on Carbon (Pd on C), palladium on alumina may be used as catalyst. Preferably Pd on C is used as it is less expensive and easier to handle.

Generally, step (i) is conducted in the presence of an organic solvent. Organic solvents which may be advantageously used include ethanol, acetone, tetrahydrofuran (THF), isopropyl alcohol, N-methylpyrrolidone (NMP), dioxane, and mixtures thereof with water. A combination of two or more organic solvents may also be used.

Advantageously, the reaction is carried out at the solvent refluxing temperature.

When Pd(PPh)3 is used, the preferred solvent is a mixture of dioxane/water 2:1 v/v, while, when Pd/C is used, the preferred solvent is ethanol.

Preferably, step (i) is conducted in the presence of a base. Bases which may be advantageously used include $Na_2CO_3$, $K_2CO_3$, $K_3PO_4$, $Cs_2CO_3$, NaOH, and KOH. The preferred base is $Na_2CO_3$.

Optionally additives such as triphenylphosphine (P(Ph$_3$)), polymethyl-hydrosiloxane (PMHS), tetrabutylammonium bromide (TBAB), 1,4-diazabicyclo-[2.2.2]octane (DABCO), or NaI may be added to the reaction medium.

Preferably, step (i) is conducted with a slight molar excess of the compound of formula (III) with respect to the compound of formula (II).

The preferred conditions for conducting the reaction of step (i) are as follows:
(a) solvent: 20 volumes ethanol;
(b) base: 2 equivalents $Na_2CO_3$;
(c) catalyst: 13% w/w Pd on C 10%.
(d) temperature: reflux.

Generally, the compound of formula (IV) is obtained in a yield higher than 70%, preferably higher than 80%. The compound of formula (IV) is preferably 3',4'-dichloro-2-fluoro-4-methyl-biphenyl.

In the second step (step ii), a compound of formula (IV) is submitted to radical bromination to form a compound of formula (V) wherein X and R are defined as above. The compound of formula (IV) may be used as a crude product or may be previously crystallized according to standard procedures.

Advantageously the radical bromination is conducted with N-bromosuccinimide (NBS) in the presence of a catalytic amount of benzoyl peroxide (PhCOO)$_2$) and acetonitrile as a solvent.

Generally, the reaction is carried out at the solvent refluxing temperature

Preferably, in order to minimise the formation of dibrominated product, step (ii) is conducted with a slight excess of NBS, preferably 1.05 mole equivalents to 1 mole equivalents of the compound of formula (IV), and in the presence of 0.04 equivalents of PhCOOO$_2$.

Generally the compound of formula (V), which is preferably 3',4'-dichloro-2-fluoro-4-bromomethyl-biphenyl, is obtained in a yield higher than 85%, preferably higher than 90%. Optionally, the compound of formula (V) may be further purified by crystallisation according to standard procedures.

In the third step (step iii) a compound of formula (V) is transformed into the corresponding nitrile compound of formula (VI) wherein X and R are defined as above.

Sodium cyanide or another suitable salt may be used. Advantageously step (iii) is conducted in an organic solvent such as ethanol or acetonitrile, preferably ethanol. The temperature used in step (iii) is preferably from about 20° C. to about 60° C., more preferably between about 40° C. and about 50° C.

Preferably, step (iii) is conducted with a molar excess of sodium cyanide. Advantageously between 1.2 mole equivalent and 1.0 mole equivalent of sodium cyanide, and preferably 1.05 mole equivalent, to 1 equivalent of compound (V) is used.

Generally the compound of formula (VI), which is preferably 3',4'-dichloro-2-fluoro-4-cyanomethyl-biphenyl, is obtained in a yield higher than 50%, preferably of about 55 to 60%.

Optionally, the compound of formula (VI) may be further purified by crystallisation according to standard procedures, preferably by slurring in ethanol.

In the fourth step (iv), a compound of formula (VI) is reacted with 1,2-dibromoethane to form a compound of formula (VII) wherein X and R are defined as above. Advantageously step (iv) is conducted in an organic solvent such as ethanol or acetonitrile or mixtures thereof with water.

Preferably the cyclopropanation step is carried out as a phase transfer catalyzed reaction in the presence of 30% NaOH and tetrabutylammonium chloride (TBAC) or tetrabutylammonium bromide (TBAB). The temperature in step (iv) is preferably maintained from about 20° C. to about 50° C.

Generally the compound of formula (VII), which is preferably 1-(3',4'-dichloro-2-fluoro[1,1'-biphenyl]-4-yl)-cyclopropanenitrile, is obtained in a yield higher than 60%, preferably of about 65 to 70%. Optionally, said compound may be further purified by crystallisation according to standard procedures, preferably using n-heptane as crystallization solvent.

In the fifth step (step v), a compound of formula (VII) is hydrolyzed to obtain the desired compound of formula (I) according to methods well known to the person skilled in the art. Preferably the hydrolysis is conducted in a mixture of methanol and water in the presence of a strong base, preferably KOH under reflux.

Generally the compound of formula (I), which is preferably 1-(3',4'-dichloro-2-fluoro[1,1'-biphenyl]-4-yl)-cyclopropanecarboxylic acid, is obtained with a yield higher than 65%.

The compound of formula (I) may be washed, filtered and isolated by various techniques known in the art. Said compound may be further purified by crystallisation according to standard procedures and is obtained with a high chemical purity, e.g. higher than 95% without using final purification by chromatography. Crystallization from a mixture of n-heptane and isopropyl alcohol is especially preferred.

The overall yield of the process is generally at least 20%, preferably equal to or higher than 25%, more preferably higher than 30%.

In a preferred embodiment, the invention provides a process for the preparation of a compound of formula (I) wherein X is fluorine and R is chlorine. In a more preferred embodiment, the invention provides a process for preparing 1-(3',4'-dichloro-2-fluoro[1,1'-biphenyl]-4-yl)-cyclopropanecarboxylic acid having formula (Ia):

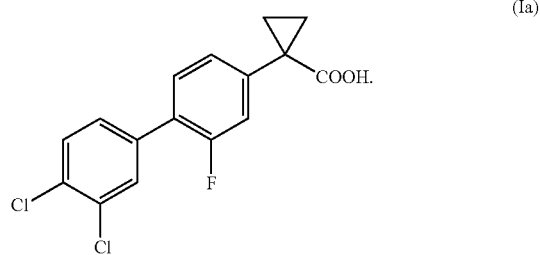

(Ia)

The obtained compound (I) may be further transformed into the corresponding pharmaceutically acceptable salts according to various techniques known in the art. Pharmaceutically acceptable salts include those in which the acidic function is reacted with an appropriate base to form, e.g., a sodium, potassium, calcium, magnesium, or ammonium salt.

The compounds of formula (I) obtained by the process of the present invention may be used in the preparation of pharmaceutical compositions for the treatment and/or the prevention of neurodegenerative diseases such as Alzheimer's disease. Such pharmaceutical compositions, preferably for the oral use, comprise at least one compound of formula (I) in admixture with at least one pharmaceutically acceptable excipient and/or carrier, for example those described in Remington's Pharmaceutical Sciences Handbook, XVII Ed., Mack Pub., N.Y., U.S.A.

Other features of the invention will become apparent in the course of the following descriptions of exemplary embodiments which are given for illustration of the invention and are not intended to be limiting thereof.

EXAMPLES

Example 1

Preparation of 3',4'-dichloro-2-fluoro-4-methyl-biphenyl 3-fluoro-4-bromotoluene (50 g, 0.265 mol) and 3,4-dichlorophenylboronic acid (53 g, 0.278 mol) were dissolved in ethanol (970 ml) and sodium carbonate (56.1 g, 0.529 mol) was added. Palladium 10% on charcoal (6.6 g) was added, and the mixture was refluxed for 4 hours under nitrogen atmosphere. The reaction mixture was cooled, filtered and concentrated, isopropyl acetate (250 ml) was added, and then the solution was concentrated again. The residue was dissolved in isopropyl acetate (250 ml) and 1M sodium hydroxide (250 ml). The organic phase was separated, washed with water (125 ml), neutralized with hydrogen chloride 3 M, washed with brine (250 ml), and concentrated. The residue was mixed with acetonitrile/water 1/1 v/v (150 ml), heated to 40° C. to dissolve and then cooled to 0 to 5° C., and stirred for 30 minutes at this temperature. The compound 3',4'-dichloro-2-fluoro-4-methyl-biphenyl crystallized as a powder.

It was filtered, washed with acetonitrile/water 1/1 v/v (25 ml), and dried at 40° C. (56 g, 86% yield).

HPLC-UV purity (210 nm): 95.0%

$^1$H NMR (DMSO-d6, 300 MHz): 7.73 (m, 2H); 7.49 (m, 2H); 7.14 (m, 2H); 2.36 (s, 3H)

Example 2

Preparation of 3',4'-dichloro-2-fluoro-4-bromomethyl-biphenyl

3',4'-dichloro-2-fluoro-4-methyl-biphenyl (29 g, 0.114 mol), N-bromosuccinimide (21.2 g, 0.119 mol), benzoyl peroxide (1.4 g, 0.004 mol) were dissolved in acetonitrile (190 ml). The mixture was refluxed for 3 hours, then cooled, mixed with a solution of sodium sulphite (2.2 g) in water (54 ml), stirred for 30 minutes and then allowed to rest to separate the phases. The lower aqueous phase was separated and extracted with dichloromethane (29 ml). The upper phase was concentrated under vacuum, mixed with water (10 ml), and dichloromethane (58 ml) and stirred. The organic phases were separated and put together, washed twice with water (29 ml), and concentrated under vacuum. The compound 3',4'-dichloro-2-fluoro-4-bromomethyl-biphenyl was isolated as an orange oil (35.7 g, 94% yield).

HPLC-UV purity (250 nm): 77.1%

$^1$H NMR (DMSO-d6, 300 MHz): 7.87-7.12 (m, 6H); 4.76 (s, 2H)

Example 3

Preparation of 3',4'-dichloro-2-fluoro-4-cyanomethyl-biphenyl

3',4'-dichloro-2-fluoro-4-bromomethyl-biphenyl (35.0 g, 0.105 mol) and sodium cyanide (5.4 g, 0.110 mol) were dissolved in a mixture of ethanol (228 ml) and water (25 ml), then heated at 50° C. for 3 hours. The solution was concentrated under vacuum and the residue was suspended in ethanol/water 1/1 v/v (35 ml) and cooled at 0-5° C. for 30 minutes. The obtained solid is filtered and dried at 40° C. under vacuum. The crude product was suspended in ethanol (56 ml) at 20 to 25° C. for 30 minutes, filtered and dried at 40° C. under vacuum. The compound 3',4'-dichloro-2-fluoro-4-cyanomethyl-biphenyl was obtained as a light brown powder (16.8 g, 57% yield).

HPLC-UV purity (250 nm): 92.3%.

$^1$H NMR (DMSO-d6, 300 MHz): 7.78 (m, 2H); 7.60 (m, 2H); 7.34 (m, 2H); 4.14 (s, 1H)

Example 4

Preparation of 1-(3',4'-dichloro-2-fluoro[1,1'-biphenyl]-4-yl)-cyclopropanenitrile 3',4'-dichloro-2-fluoro-4-cyanomethyl-biphenyl (9.0 g, 0.032 mol), 1,2-dibromomethane (9.0 g, 0.048 mol), 1.2 tetrabutylammonium chloride (1.2 g, 0.043 mol), toluene (60 ml), and water (9 ml) were loaded in a reactor. Sodium hydroxide 30% aq. (60 g, 0.45 mol) was added drop-wise over 30 minutes at 20 to 25° C. and the reaction mixture was stirred for 6 hours. The organic phase was separated, washed with water (12 ml), with hydrogen chloride 3 M aq. (36 ml) and finally with water (12 ml). The solution was concentrated, then n-heptane (18 ml) was added at 80° C. The solution was cooled to 0 to 5° C. and stirred for 30 minutes. The product crystallized from solution, it was filtered, washed with cold n-heptane (5 ml) and dried at 40° C. under vacuum. The compound 1-(3',4'-dichloro-2-fluoro[1,1'-biphenyl]-4-yl)-cyclopropanenitrile was obtained as a yellow powder (6.4 g, 65% yield).

HPLC-UV purity (250 nm): 98.2%.

$^1$H NMR (DMSO-d6, 300 MHz): 7.78 (m, 2H); 7.60 (m, 2H); 7.30 (m, 2H); 1.84 (m, 2H); 1.63 (m, 2H).

Example 5

Preparation of 1-(3',4'-dichloro-2-fluoro[1,1'-biphenyl]-4-yl)-cyclopropane carboxylic acid 1-(3',4'-dichloro-2-fluoro[1,1'-biphenyl]-4-yl)-cyclopropanenitrile (14.3 g, 0.047 mol) was dissolved in a mixture of methanol (143 ml) and water (71.5 ml), potassium hydroxide (35.1 g, 0.563 mol) was added portion-wise, and the mixture was refluxed for 48 hours. The reaction mixture was cooled and poured in a solution of aqueous hydrogen chloride 36% (57 ml) in water (57 ml) at 20 to 25° C. The suspension was stirred and filtered; the solid was repeatedly washed with water and dried at 40° C. under vacuum. The crude product was dissolved in refluxing 2-propanol (178 ml), the solution was mixed with activated carbon (0.3 g), stirred at reflux and filtered, concentrated and mixed with n-heptane (116 ml). The hot solution was cooled to 0 to 5° C. and the crystallized solid was filtered, washed with 2-propanol, and dried at 40°

C. under vacuum. The compound 1-(3',4'-dichloro-2-fluoro[1,1'-biphenyl]-4-yl)-cyclopropanecarboxylic acid was obtained as a white powder (10.3 g, 68% yield).

HPLC-UV purity (255 nm): 99.8%

$^1$H NMR (DMSO-d6, 300 MHz): 12.51 (bs, 1H); 7.78 (m, 2H); 7.54 (m, 2H); 7.30 (m, 2H); 1.48 (m, 2H); 1.22 (m, 2H)

MS (ESI$^-$, 40 V): 323 (M$^-$); 279.

Melting range: 199-200° C.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing a compound represented by formula (Ia) or a pharmaceutically acceptable salt thereof:

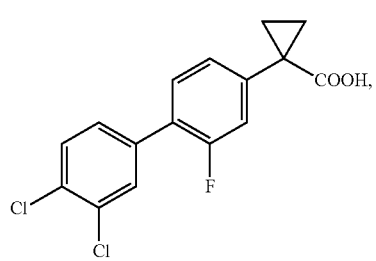

(Ia)

said process comprising:
(i) reacting a compound represented by formula (IIa):

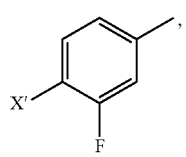

(IIa)

wherein X' is selected from the group consisting of chlorine, bromine, iodine, and a triflate group, with a compound represented by formula (IIIa):

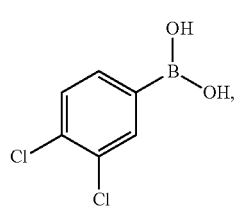

(IIIa)

to obtain a compound represented by formula (IVa):

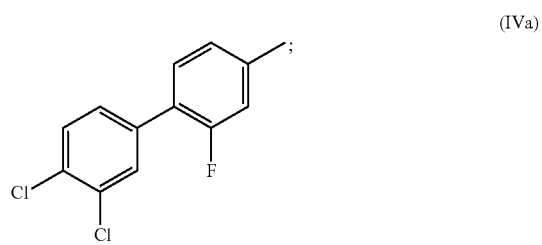

(IVa)

(ii) submitting said compound represented by formula (IVa) to radical bromination to obtain a compound of formula (Va):

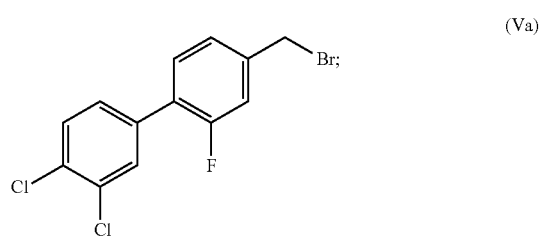

(Va)

(iii) transforming said compound represented by formula (Va) into a nitrile compound represented by formula (VIa):

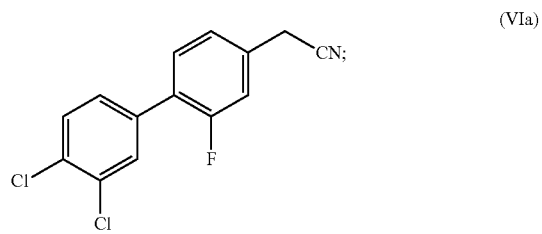

(VIa)

(iv) reacting said compound represented by formula (VIa) with 1,2-dibromoethane to obtain a compound represented by formula (VIIa):

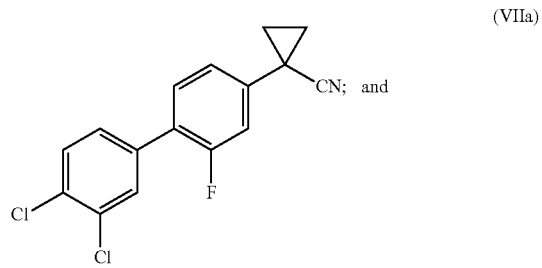

(VIIa)

(v) hydrolyzing said compound represented by formula (VIIa) to obtain said compound represented by formula (Ia) or a pharmaceutically acceptable salt thereof.

2. A process as claimed in claim 1, further comprising:
(vi) isolating and crystallising said compound represented by formula (Ia) or a pharmaceutically acceptable salt thereof.

3. A process according to claim 2, wherein said said compound represented by formula (Ia) or a pharmaceutically acceptable salt thereof is crystallized from a solvent which comprises a mixture of n-heptane and isopropyl alcohol.

4. A process as claimed in claim 1, wherein said reacting said compound represented by formula (IIa) with said compound represented by formula (IIIa) is conducted in the presence of at least one palladium catalyst selected from the group consisting of tetrakis(triphenylphosphine)palladium, palladium on activated charcoal, and palladium on alumina.

5. A process as claimed in claim 2, wherein said reacting said compound represented by formula (IIa) with said compound represented by formula (IIIa) is conducted in the presence of at least one palladium catalyst selected from the group consisting of tetrakis(triphenylphosphine)palladium, palladium on activated charcoal, and palladium on alumina.

6. A process as claimed in claim 1, wherein said reacting said compound represented by formula (IIa) with said compound represented by formula (IIIa) is conducted in the presence palladium on activated charcoal.

7. A process as claimed in claim 2, wherein said reacting said compound represented by formula (IIa) with said compound represented by formula (IIIa) is conducted in the presence palladium on activated charcoal.

8. A process as claimed in claim 3, wherein said reacting said compound represented by formula (IIa) with said compound represented by formula (IIIa) is conducted in the presence palladium on activated charcoal.

9. A process as claimed in claim 1, wherein said submitting said compound represented by formula (IVa) to radical bromination comprises reacting said compound represented by formula (IVa) with N-bromosuccinimide in the presence of a catalytic amount of benzoyl peroxide in a solvent which comprises acetonitrile.

10. A process as claimed in claim 2, wherein said submitting said compound represented by formula (IVa) to radical bromination comprises reacting said compound represented by formula (IVa) with N-bromosuccinimide in the presence of a catalytic amount of benzoyl peroxide in a solvent which comprises acetonitrile.

11. A process as claimed in claim 3, wherein said submitting said compound represented by formula (IVa) to radical bromination comprises reacting said compound represented by formula (IVa) with N-bromosuccinimide in the presence of a catalytic amount of benzoyl peroxide in a solvent which comprises acetonitrile.

12. A process as claimed in claim 4, wherein said submitting said compound represented by formula (IVa) to radical bromination comprises reacting said compound represented by formula (IVa) with N-bromosuccinimide in the presence of a catalytic amount of benzoyl peroxide in a solvent which comprises acetonitrile.

13. The compound 1-(3',4'-dichloro-2-fluoro[1,1'-biphenyl]-4-yl)-cyclopropanenitrile or a salt thereof.

14. A process for preparing a pharmaceutical composition, comprising:
   preparing 1-(3',4'-dichloro-2-fluoro[1,1'-biphenyl]-4-yl)-cyclopropanecarboxylic acid or a pharmaceutically acceptable salt thereof by a process according to claim 1; and
   combining said 1-(3',4'-dichloro-2-fluoro[1,1'-biphenyl]-4-yl)-cyclopropanecarboxylic acid or a pharmaceutically acceptable salt thereof with one or more pharmaceutically acceptable excipients.

\* \* \* \* \*